United States Patent [19]

Suzuki et al.

[11] Patent Number: 4,971,956
[45] Date of Patent: Nov. 20, 1990

[54] IMMUNOPOTENTIATING AGENTS AND METHOD

[75] Inventors: Shigeo Suzuki; Masuko Suzuki, both of Sendai; Hitoshi Katayama, Kodaira, all of Japan

[73] Assignee: Ihara Chemical Industry Co., Ltd., Tokyo, Japan

[21] Appl. No.: 363,307

[22] Filed: Jun. 7, 1989

Related U.S. Application Data

[63] Continuation of Ser. No. 258,079, Oct. 14, 1988, abandoned, which is a continuation of Ser. No. 800,774, Nov. 22, 1985, abandoned.

[30] Foreign Application Priority Data

Nov. 29, 1984 [JP] Japan ................................ 59-252761
Mar. 15, 1985 [JP] Japan ................................ 60-50618
May 22, 1985 [JP] Japan ................................ 60-109854

[51] Int. Cl.$^5$ .......................................... A61K 31/73
[52] U.S. Cl. ..................................................... 514/55
[58] Field of Search ............................................ 514/55

[56] References Cited

U.S. PATENT DOCUMENTS

3,914,413 10/1975 Balassa .
4,605,623 8/1986 Malette et al. ........................ 514/55

FOREIGN PATENT DOCUMENTS

| 105106A | 8/1983 | European Pat. Off. | ............ 424/180 |
| 105106 | 4/1984 | European Pat. Off. | ............ 424/180 |
| 183556 | 6/1986 | European Pat. Off. | ............ 514/55 |
| 127824 | 11/1978 | Japan | ............ 514/55 |
| 41326 | 4/1979 | Japan | ............ 514/55 |
| 9027826 | 10/1982 | Japan | ............ 424/180 |
| 27826 | 2/1984 | Japan | ............ 424/180 |
| 142923 | 7/1985 | Japan | ............ 514/55 |

OTHER PUBLICATIONS

The Merck Index 10th ed, 2017 (1983).
Chemical Abstracts 102: 84445j (Ajnomoto).
Chemical Abstracts 76: 35410a (1972).
Jnl of American Chemical Society 79, 5046–5049 (1957).
Proceedings of the National Academy of Sciences, vol. 74 (1) Jan. 1977, Kieda et al.
*Patent Abstracts of Japan*, Unexamined Applications, Section C, vol. 4, No. 77, Jun. 4, 1980.
*Journal of the Chemical Society*, Section C, Part II, 1970, London, Capon et al., pp. 1654–1655.

*Primary Examiner*—Douglas W. Robinson
*Assistant Examiner*—Zohreh A. Fay
*Attorney, Agent, or Firm*—Larson & Taylor

[57] ABSTRACT

A new immunopotentiating agent is now provided, which is useful for enhancing the immune response in living animals, including man, against the bacterial and fungan infections and also against the growth of tumors, and which comprises as active ingredient a water-soluble chitin-oligomer selected from di-N-acetyl-chitobiose, tri-N-acetyl-chitotriose, tetra-N-acetyl-chitotetraose, penta-N-acetyl-chitopentaose, hexa-N-acetyl-chitohexaose and hepta-N-acetyl-chitoheptaose, or a water-soluble chitosan-oligomer selected from chitobiose, chitotriose, chitotetraose, chitopentaose, chitohexaose and chitoheptaose. An immunopotentiating method using said water-soluble chitin-oligomer or said water-soluble chitosan-oligomer as the active ingredient is also provided.

2 Claims, No Drawings

IMMUNOPOTENTIATING AGENTS AND METHOD

This application is a continuation of application Ser. No. 258,079 filed Oct. 14, 1988 which is a continuation of application Ser. No. 800,774 filed Nov. 22, 1985, both now abandoned.

SUMMARY OF THE INVENTION

This invention relates to a new immunopotentiating agent comprising a chitin-oligomer or a chitosan-oligomer as the active ingredient which is useful as the host defense stimulator to enhance the immune response in living animals, including man. This invention also relates to a method for stimulating the immune response.

BACKGROUND OF THE INVENTION

Hithertofore, various known antibiotics and antibacterial or antifungal chemical compounds have been used as the agents for controlling or treating therapeutically bacterial or fungal infections. However, some of the known antibiotics and antibacterial chemical compounds can often give side-effects in the patients treated during the therapeutic treatment of bacterial infections due to occurrence of mutation of the microbial strains which are resistant to the antibiotics and/or the antibacterial chemical compounds as administered. In these circumstances, a lasting demand for a new antibacterial or antifungal agent exists. Besides, it is known that such patients having lower immune function than their normal level of the immune function, for example, the tumor-bearing patients and such patients whose immune response has been reduced to an abnormally reduced level by preliminary administration of an immunosuppressive agent before surgical operations for the purpose of facillitating the transplantation of internal organs, are highly susceptible to the opportunistic infection by bacteria and fungi, so that a demand for such a new immunopotentiating agent effective to control and/or treat therapeutically the bacterial and fungal infections is also seen. We, the present inventors, recently have provided such a series of new agents for therapeutic control and treatment of bacterial and fungal infections, which comprise chitin or chitosan as the active ingredients exhibiting the immunopotentiating activities to meet the above-mentioned demands (Japanese patent application first publication "Kokai" Sho No. 59-27827, laid open on 14th February, 1984). Chitin and chitosan are readily available as they occur in large quantities in nature, for instance, in the cell walls of microorganisms and in the outer shells of insects, and Crustacea such as crabs and lobsters.

On the other hand, several agents for therapeutic treatment of malignant tumors which comprise as the active ingredient a polysaccharide or polysaccharides isolated from the cells of microorganisms or from the metabolic products of microorganisms have been proposed in recent years. For example, lentinan, namely such a polysaccharide isolated from the fruit body of a mushroom called "shiitake" (*Cortinellus shiitake*) (see Japanese patent publication Nos. 37002/72 and 484/74), an antitumor polysaccharide-protein complex as isolated from a mushroom called "kawaratake" in Japan (*Coriolus versicolor*) (see Japanese patent publication Nos. 23271/80 and 40159/82, U.S. Pat. Nos. 4,271,151, 4,289,688, U.K. Pat. No. 1,565,090 and Canadian Pat. No. 1,084,488), and an antitumor agent comprising the active ingredient such as lipo-polysaccharides isolated from the cell wall of *Mycobacterium tuberculosis* which is virulent to man(see Japanese patent application first publication "Kokai" Sho No. 57-18619, laid open on 30th January, 1982). We, the present inventors, have also provided an antitumor agent comprising as the active ingredient chitin which is a polysaccharide composed of N-acetylglucosamine residues and exists in large quantities in nature (see Japanese application first publication "Kokai" Sho No. 59-27826, laid open or 14th February, 1984 and the "Microbiology and Immunology" 2, 93, 1984).

The above-mentioned therapeutic agents comprising chitin or chitosan as the active ingredient have remarkable therapeutic activities for control and treatment of the bacterial and fungal infections and for the treatment of tumors. However, both chitin and chitosan are difficult to be formulated into injectable aqueous solutions for intravenous administration because chitin and chitosan are water-insoluble polymers, and hence they are not yet entirely satisfactory in practice to be used in the therapeutic treatment of bacterial and fungal infections and also in the therapeutic treatment of tumors in clinic.

We have made further researches in an attempt to overcome the above-mentioned disadvantages of the chitin and chitosan when used as the antibacterial and antifungal agents and as the antitumor agent. As a result, we have now found unexpectably that several water-soluble chitin-oligomers (otherwise termed as the N-acetyl-chito-oligosaccharides) which are known as the hydrolysis products of chitin, and several water-soluble chitosan-oligomers (otherwise termed as the chito-oligosaccharides) which are also known as the hydrolysis products of chitosan, possess the immunopotentiating activities to stimulate and enhance the immune response in host animals, and are also able to exhibit the inhibitory effects against the infections of bacteria and fungi, as well as the antitumor activity in the same host animals.

The water-soluble chitin-oligomers of which the immunopotentiating activities have now been discovered by us are represented by the following general formula (Ia)

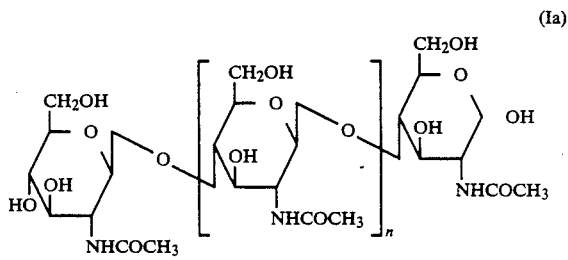

wherein n is an integer of from zero to 5; n is zero for di-N-acetyl-chitobiose, n is 1 for tri-N-acetyl-chitotriose, n is 2 for tetra-N-acetyl-chitotetraose, n is 3for penta-N-acetyl-chitopentaose, n is 4 for hexa-N-acetyl-chitohexaose and n 5 for hepta-N-acetyl-chitoheptaose.

The water-soluble chitosan-oligomers of which the imunopotentiating activities have now been discovered by us are represented by the following general formula (Ib)

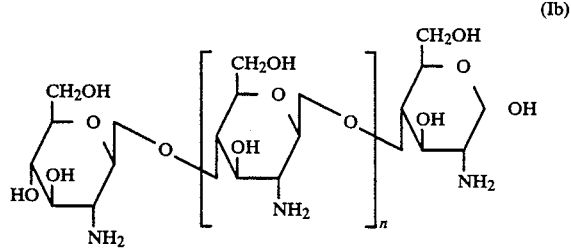

(Ib)

wherein n is an integer of from zero to 5; n is zero for chitobiose, n is 1 is for chitotriose, n is 2 for chitotetraose, n is 3 for chitopentaosne, n is 4 for chitohexaose and n is 5 for chitoheptaose.

Based on our above findings, we have accomplished this invention.

Production and some properties of the chitin-oligomers are described in the "Journal of Chemical Society (C)", 1970, pages 1654–1655, and production and some properties of the chitosan-oligomers are described in the "Journal of American Chemical Society", 79, 5046–5049, 1957, for example.

DETAILED DESCRIPTION OF THE INVENTION

According to the first aspect of this invention, therefore, there is provided an immunopotentiating agent comprising as the active ingredient a water-soluble chitinoligomer selected from di-N-acetyl-chitobiose, tri-N-acetylchitotriose, tetra-N-acetyl-chitotetraose, penta-N-acetylchitopentaose, hexa-N-acetyl-chitohexaose and hepta-N-acetylchitoheptaose, or a water-soluble chitosan-oligomer selected from chitobiose, chitotriose, chitotetraose, chitopentaose, chitohexaose and chitoheptaose, in combination with a pharmaceutically acceptable carrier for the active ingredient.

The immunopotentiating agent of this invention may be in the form of a pharmaceutical composition comprising one or more of said immunopotentiating chitinoligomers and chitosan-oligomers as the active ingredient in an immunopotentiating effective amount thereof, in admixture with a pharmaceutically acceptable liquid or solid carrier which is known and usually employed in the formulation of medicines, such as physiological saline, starch and talc. Amongst the above-mentioned particular examples of the immunopotentiating chitinoligomers and chitosan-oligomers, penta-N-acetylchitopentaose and hexa-N-acetyl-chitohexaose are preferred, and the latter compound is most preferred because of its highest effects.

The immunopotentiating agent of this invention may advantageously be formulated into an injectable aqueous solution of its active ingredient compound in a conventional manner, utilizing the high water-solubility of the chitin-oligomer or chitosan-oligomer employed as the active ingredient. The injectable aqueous solution so prepared may be administered not only intravenously but also subcutaneously, intracutaneously, intramuscularly or intraperitoneally. The immunopotentiating agent of this invention may also be formulated into tablets or powders for oral administration by admixing with a pharmaceutically acceptable known solid carrier. The injectable aqueous solution so prepared may contain 0.1% to 10% by weight of the chitin-oligomer of the formula (Ia) or the chitosan-oligomer of the formula (Ib). The immunopotentiating agent of this invention in the form of tablets or powders may contain 10% to 30% by weight of the chitin-oligomer of the formula (Ia) or the chitosan-oligomer of the formula (Ib).

We have now experimentally confirmed that the chitin-oligomers of the formula (Ia) and the chitosanoligomers of the formula (Ib) shown hereinbefore, particularly penta-N-acetyl-chitopentaose, hexa-N-acetyl-chitohexaose, hepta-N-acetyl-chitoheptaose, chitopentaose, chitohexaose and chitoheptaose, exhibit such remarkable effects of activating the active oxygen-generating capacity and the chemotactic activity of phagocytes in mice when they are intraperitoneally administered to the mice. Thus, we have firstly observed that when the oligomers of the formula (Ia) and (Ib), especially penta-N-acetyl-chitopentaose, hexa-N-acetylchitohexaose, hepta-N-acetyl-chitoheptaose, chitopentaose, chitohexaose and chitoheptaose are administered intraperitoneally to mice which had been lethally infected with true fungi (Eumycetes), particularly *Candida albicans,* gram-negative bacteria such as *Pseudomonas aeruginosa,* or with gram-positive bacteria such as *Staphylococcus aureus* and *Listeria monocytogenes,* the life span of the infected mice so treated is elongated, as compared with the life span of the infected mice untreated, in spite of the fact that the above mentioned particular chitin-oligomers and chitosan-oligomers by themselves are not inhibitory to the growth of the fungi and bacteria in vitro. This appeared to reveal that the chitin-oligomers of the formula (Ia) and the chitosan-oligomers of the formula (Ib) exhibit in vivo the immunopotentiating activity for enchancing the immune response in the host mice through some biological mechanism. Therefore, we have experimentally investigated the mechanism for the immunopotentiation and have confirmed that the oligomers of the formula (Ia) and (Ib) exert the effects of activating the active oxygen-generating capacity and the chemotactic activity of phagocytes in vivo, thus promoting the activity of the phagocytes to kill the infecting fungi and bacteria.

According to an embodiment of the first aspect of this invention, therefore, there is provided an immunopotentiating agent which is used for enhancing the immune response against the bacterial and fungal infections, and which comprises an effective amount of the chitin-oligomer of the formula (Ia) or chitosan-oligomer of the formula (Ib), especially penta-N-acetyl-chitopentaose, hexa-N-acetyl chitohexaose, hepta-N-acetylchitoheptaose, chitopentaose, chitohexaose or chitoheptaose, in combination with a pharmaceutically acceptable carrier for the active ingredient. For this antibacterial and antifungal purpose, the agent of this invention is effective especially to control the infection with *Candida albicans, Pseudomonas aeruginosa, Staphylococcus aureus* and *Listeria monocytogenes.* The active ingredient compounds may be administered at the effective dosage from 1 to 200 mg/kg, preferably from 10 to 150 mg/kg per day.

Moreover, we have experimentally found that all the particular twelve compounds as included by the chitinoligomers of the formula (Ia) and by the chitosan-oligomers of the formula (Ib) are active to promote the cellular immunity, i.e., the cell-mediated immunity as well as humoral immunity in mice and other living animals, including man, and are thus active to stimulate and enhance the immune response in host animals inhibitorily to the growth of tumors. It has also been revealed that the immunopotentiating agent of this invention is effective as an antitumor agent for inhibiting the growth of tumors, including various mouse cancer cells such as Sarcoma-180, Ehrlich carcinoma, MM-46 and Meth-A.

According to a further embodiment of the first aspect invention, therefore, there is provided an immunopotentiating agent which is used for enhancing the immune response against the growth of tumors, and which comprises an effective amount of a chitin-oligomer of the formula (Ia) or a chitosanoligomer of the formula (Ib), preferably tetra-N-acetylchitotetraose, penta-N-acetyl chitopentaose, hexa-N-acetylchitohexaose, hepta-N-acetyl-chitoheptaose, chitotetraose, chitopentaose, chitohexaose or chitoheptaose, in combination with a pharmaceutically acceptable carrier. For the purpose of cancer immunotherapy, the active ingredient compound of the formula (Ia) or (Ib) may be administered at the effective dosages from 1 to 500 mg/kg, preferably from 10 to 150 mg/kg per day.

The immunopotentiating agent of this invention, when used as the antitumor agent, is advantageous in that the chitin-oligomers of the formula (Ia) or the chitosan-oligomers of the formula (Ib) used as the active ingredient are very much safe to human, because they are substantially not toxic to human and do not exhibit any side-effects in practice when administered to human; that the water-soluble chitin-oligomers and chitosan-oligomers are readily formulatable into injectable aqueous solution and hence easily administrable to human, that the development of their therapeutic effects after the administration of the agent of this invention is fast; that the agent of this invention may be formulated into the intravenously injectable preparation into which the previously known anti-tumor agents comprising the high-molecular polysaccharides, including those of the chitin and chitosan as the active ingredient are practically impossible to be formulated; and that the active oligomer compounds to be used in the agent of this invention may readily be isolated and purified to a pure product owing to their relatively simple chemical structure and their low molecular weights.

Furthermore, we have found that the chitin-oligomers of the formula (Ia) or the chitosan-oligomers of the formula (Ib) are also effective as adjuvants when administered together with an antigen given as a vaccine, in the sense that the effects of the immunity induced by the vaccine antigen as administered into a host animal can be enhanced by concurrent administration of the chitin-oligomers of the formula (Ia) or the chitosan-oligomers of the formula (Ib). Whether the chitin-oligomers of the formula (Ia) or the chitosan-oligomers of the formula (Ib) are able to serve either as the adjuvant or as the immunopotentiating agent, it may be demonstrated, as known to the expert, by showing that intraperitoneal injection of the chitin-oligomers or the chitosan-oligomers to the mice having been immunized with intravenously injected sheep red blood cells (SRBC) as antigen can increase the number of the antibody-forming cells in spleen cells of the treated mice in term of the number of the plaque-forming cells as enumerated by Jerne's hemolytic plaque assay (see N. K. Jerne, A. A. Nordin and C. Henrry: "The agar plaque technique for recognizing antibody-producing cells. Cell bound Antibodies." ed. B.Amos and H.Koprowski pp. 109–122, Wister Institute Press. Philadelphia, 1963). It was also demonstrated that the chitin-oligomers or the chitosan-oligomers can enhance the cellular immunity in mice as estimated by delayed-type hypersensitivity (D.T.H.) to SRBC according to the method of Lagrange et al (see P. H. Lagrange, G. B. Mackaness and T. E. Miles "J. Exp. Med." 139, 1529–1539, 1974). When the immunopotentiating agent of this invention is applied as adjuvants comprising the chitin-oligomer of the formula (Ia) or the chitosan-oligomer of the formula (Ib), these potentiators can be uptaken easily into the host body owing to its high water-solubility and can enhance the cellular and humoral immunities but give neither substantial toxicity nor side-effects, in contrast to that displayed by some known adjuvants such as alum and aluminum phosphate as well as oily Freund adjuvants containing Bayol F and Drakeol, which were found to be hardly uptaken after injection and often give rise to a long lasting induration at the injection sites of the adjuvants.

According to the second aspect of this invention, there is provided a use as an immunopotentiating agent of a water-soluble chitin-oligomer selected from di-N-acetyl-chitobiose, tri-N-acetyl-chitotriose, tetra-N-acetyl-chitotetraose, penta-N-acetyl-chitopentaose, hexa-N-acetyl-chitohexaose and hepta-N-acetyl-chitoheptaose, or of a water-soluble chitosan-oligomer selected from chitobiose, chitotriose, chitotetraose, chitopentaose, chitohexaose and chitoheptaose.

As far as we are aware of, the water-soluble chitin-oligomers of the formula (Ia) and the water-soluble chitosan-oligomers of the formula (Ib) were never used as any medicine. According to the third aspect of this invention, therefore, there is provided a pharmaceutical composition comprising a water-soluble chitin-oligomer selected from di-N-acetylchitobiose, tri-N-acetyl-chitotriose, tetra-N-acetyl-chitotetraose, penta-N-acetyl-chitopentaose, hexa-N-acetylchitohexaose, hepta-N-acetyl-chitoheptaose, or a watersoluble chitosan-oligomer selected from chitobiose, chitotriose, chitotetraose, chitopentaose, chitohexaose and chitoheptaose, as the active ingredient.

According to another aspect of this invention, there is provided a method for stimulating the immune response, which comprises administering an immunopotentiatingly effective amount of a water-soluble chitin-oligomer selected from di-N-acetyl-chitobiose, tri-N-acetyl-chitotriose, tetra-N-acetyl-chitotetraose, penta-N-acetyl-chitopentaose, hexa-N-acetyl-chitohexaose, hepta-N-acetyl-chitoheptaose, or of a water-soluble chitosan-oligomer selected from chitobiose, chitotriose, chitotetraose, chitopentaose, chitohexaose and chitoheptaose, to a host animal of which the immunity is desired to be enhanced.

According to a further aspect of this invention, there is provided a method of controlling bacterial and fungal infections in a living animal including man, which comprises administering to the infected host animal tetra-N-acetyl-chitotetraose, penta-N-acetyl-chitopentaose, hexa-N-acetyl-chitohexaose, hepta-N-acetyl-chitoheptaose, chitotetraose, chitopentaose, chitohexaose or chitoheptaose in an effective amount thereof to enhance the immune response of the animal against the bacterial and fungal infections.

Moreover, it is known that some of the therapeutic agents such as antibiotics, medicinal drugs, antitumor drugs and hormones may be encapsuled in the liposomes which are unilamellar or multilamellar phospholipid vesicles, and that the liposomes serve as the carrier vesicles for the therapeutic agent entrapped therein and also give rise to an improved uptake of the therapeutic agent by the target organs or tissues in vivo after the administration (see, for example, an article titled "New Aspects of Liposomes" in the "Biochimica et Biophysica Acta," 457, 259-302, 1976; the "Proc. Natl. Acad. Sci. U.S.A." 73, No. 5, 1603-1607, 1976; and the "Cancer Research" 39, 881-892, 1979). We have now further found that when any of the chitin-oligomers of the formula (Ia) or the chitosan-oligomers of the formula (Ib) is encapsuled in the known liposomes, said oligomer can exhibit further improved immunopotentiating activities to inhibit the growth of tumors and to control the bacterial and fungal infections. The liposome formulation containing the chitin-oligomer of the formula (Ia) or the chitosan-oligomer of the formula (Ib) in the phospholipid vesicles may be prepared according to the known techniques for the preparation of the liposome formulations. The liposomes for encapsulation of the chitin-oligomer or the chitosan oligomer may usually be composed of the known unilamellar vesicles or multilamellar vesicles made of the film-forming phospholipid material, including natural phospholipids such as phosphatidylcholine (that is, lecithin), phosphatidylethanolamine, phosphatidylserine, phosphatidylinositol, phosphatidylglycerol and sphingomyeline, as well as synthetic phospholipids such as dipalmitoylphosphatidylcholine, distearoylphosphatidylcholine and dipalmitolylphosphatidylethanolamine. If desired, the film-forming phospholipid materials may be admixed with an appropriate proportion of a conventional stabilizer, for example, cholesterol, dicetyl phosphate, phosphatidic acid, stearylamine and other electrically charged lipids, as well as $\alpha$-tocopherol and the like.

An available process for preparing the liposomes containing the chitin-oligomer or the chitosan-oligomer entrapped therein may comprises, for instance, the steps of placing in a vessel a solution of the liposome film-forming phospholipid material in an organic solvent such as chloroform and ethanol, evaporating in vacuo entirely or partially the organic solvent from the phospholipid solution in said vessel to produce solid thin films of the phospholipid material on the inner wall surface of the vessel, subsequently charging into the vessel a solution of the active chitin-oligomer or chitosan-oligomer in water, physiological saline, buffered phosphate solution, buffered tris-aminomethane solution or in an aqueous solution of glucose or sorbitol and the like, and agitating the whole contents in the vessel mechanically or under ultrasonic actions, until the liquid suspension of the liposomes is formed. Or, the liposome formulations may also be produced, for example, by mixing an aqueous solution of the chitin-oligomer or the chitosan-oligomer with a solution of the liposome film-forming phospholipid material in a water-immiscible organic solvent such as diethylether and diisopropylether, emulsifying the resultant liquid mixture by mechanical agitation or under ultrasonic actions, and then evaporating in vacuo entirely or partially the organic solvent from the resultant emulsion so that the suspension of the liposomes is formed.

The liposomes present in the suspension so obtained may then be purified by isolating the particles of the liposomes from the liquid medium of said suspension by centrifugation, re-dispersing the isolated particulate liposomes into an aqueous liquid medium in which the chitin-oligomer or the chitosan-oligomer is soluble, and then separating the liposome particles centrifugally from the dispersion so obtained. The first prepared suspension of the liposomes may also be passed through a column of a gel-filtration agent such as Sephadex for the purification purpose.

The liposomes containing the chitin-oligomer or the chitosan-oligomer so purified may be handled as such in the form of liquid suspension mentioned above. The particulate liposomes as isolated may be redispersed in an appropriate liquid medium for ready use. Alternatively, the suspension of the liposomes may be freeze-dried to separate the particles of the liposomes which are then again dispersed in an appropriate liquid medium. In any way, the liposomes containing the chitin-oligomer or the chitosan-oligomer may be formulated as an intravenously or intraperitoneally injectable preparation in the form of a dispersion in an appropriate aqueous liquid medium. The chitin-oligomer of the formula (Ia) or the chitosan-oligomer of the formula (Ib) as the liposome formulation may be administered at a dosage of said oligomer of 1 mg/kg to 500 mg/kg, preferably of 10 mg/kg to 150 mg/kg per day, when it is given for the antitumor treatment by the immunopotentiation. While, the chitin-oligomer of the formula (Ia) or the chitosan-oligomer of the formula (Ib) as the liposome formulation may be administered as a dosage of said oligomer of 1 mg/kg to 100 mg/kg per day, when it is given for the purpose of controlling the bacterial and fungal infections through the immunopotentiating activities of the chitin-oligomer or the chitosan-oligomer.

This invention in now illustrated with reference to the following Examples.

EXAMPLE 1

This Example illustrates the manufacture of an injectable solution of penta-N-acetyl-chitopentaose.

Penta-N-acetyl-chitopentaose (10 g) was dissolved in an appropriate volume of a physiological saline as prepared for the injection use, to a total volume of 1000 ml. The resulting solution was formulated into the injectable solution preparation according to the standard method of preparing the injectable formulations as stipulated in the 10th Japanese Pharmacopoeia.

EXAMPLE 2

This Example illustrates the manufacture of an injectable solution of hexa-N-acetyl-chitohexaose.

Hexa-N-acetyl-chitohexaose (10 g) was dissolved in an appropriate volume of a physiological saline as prepared for the injection use, to a total volume of 1000 ml. The resulting solution was formulated into the injectable solution preparation in the same manner as in Example 1.

EXAMPLE 3

This example illustrated the manufacture of an injectable solution of chitohexaose.

Chitohexaose (10 g) was dissolved in an appropriate volume of a physiological saline as prepared for the injection use, to a total volume of 1000 ml. The resulting solution was formulated into the injectable solution preparation in the same manner as in Example 1.

EXAMPLE 4

This Example demonstrates that tetra-N-acetyl-chitotetraose, penta-N-acetyl-chitopentaose, and hexa-N-acetyl-chitohexaose exhibit the activities of promoting the active oxygen-producing capacity of peritoneal macrophages existing in the peritoneal exudate cells of mice, indicating that the compounds under test can enhance the phagocytic activities of the macrophages as one function of the immunopotentiating activities of the tested compounds.

An injectable solution of tetra-N-acetyl-chitotetraose, penta-N-acetyl-chitopentaose or hexa-N-acetyl-chitohexaose as prepared similarly to the Example 1 to 3 above was intraperitoneally injected into BALB/C mice (male, 4 to 6 weeks-aged, 8 mice per group) at a dosage of the active ingredient of 50 mg/kg. At the times of 3, 12, 24 and 48 hours after the injection the peritoneal cavities of the treated mice were washed with Hanks' buffered solution, the washings were combined together and the peritoneal exudate cells were separated therefrom. The periotoneal exudate cells so collected were suspended in a fresh Hanks' buffered solution to a concentration of $1 \times 10^6$ cells per ml. The resulting suspension of the peritoneal exudate cells was mixed with 5 mmol glucose and 50 $\mu$l of a solution of 2 mg/ml of luminol in dimethylsulfoxide, and the mixture obtained was incubated for 10 minutes at 37° C. The chemiluminescence response in the incubated mixture was determined over 10 minutes by means of a chemiluminescence measuring apparatus, Biolumat LB9500 (Berthold Co., West Germany).

It was assumed that the intensity (cpm) in the chemiluminescence response as determined was substantially proportional to the intensity in the active oxygen-generating capacity and hence the intensity in the phagocytic activities of the macrophages of the peritoneal exudate cells which would be promoted by the administration of the water-soluble chitin-oligomer under test, so that the determination of the intensity in the chemiluminescence response of said incubated mixture would indicate such enhanced phagocytic activities of the macrophages of the peritoneal exudate cells as induced by the chitin-oligomer.

The above experiments were carried out in the same manner as above, using the physiological saline containing no test compound and also using the chitin, the parent polysaccharide.

The results of test in term of an average value±standard deviation are summarized in Table 1.

TABLE 1

Chemiluminescence response in Peritoneal Exudate Cells in Mice Intraperitoneally Administered with the Chitin-oligomer or with Comparative Compounds

| Experiment No. | Test compound | Chemiluminescence response (cpm) |
|---|---|---|
| 1 | Tetra-N-acetyl-chitotetraose | 40948 ± 11083 ($\underline{P}$ <0.05*) |
| 2 | Penta-N-acetyl-chitopentaose | 141162 ± 55098 ($\underline{P}$ <0.01**) |
| 3 | Hexa-N-acetyl-chitohexaose | 443649 ± 135766 ($\underline{P}$ <0.01**) |
| 4 (Comparative test) | Chitin | 121720 ± 23354 $\underline{P}$ <0.01** |
| Control test | None (Physiological saline) | 7493 ± 1174 |

In Table 1, the asterisked term "P<0.05" denotes that error probability in the results of test are less than 5% as measured by the known Student's "t" analysis, and the double asterisked term "P<0.01" denotes that the error probability in the results of test were less than 5% in the same meaning as above, herein and hereinafter unless otherwise stated.

EXAMPLE 5

This Example demonstrates that the candidacidal activity of the peritoneal exudate cells of the mice intrapertioneally administered with the chitin-oligomers is enhanced. This Example also indicates that the chitin-oligomers can promote the candida-killing activities of the macrophages in the peritoneal exudate cells from the treated mice.

An injectable solution as prepared similarly to the Examples 1-3 containing a chitin-oligomer indicated in Table 2 was intraperitoneally administered to BALB/C mice (male, 4 to 6 weeks-aged, 8 mice per group) at a dosage of the active ingredient of 50 mg/kg. At the times of 3, 12, 24 and 48 hours after the injection of the tested chitinoligomer, the peritoneal cavities of the treated mice were washed with Hanks' buffered solution, then the washings were combined together and the peritoneal exudate cells were collected therefrom by centrifugation. The peritoneal exudate cells were suspended in a fresh Hanks' buffered solution to a concentration of $1 \times 10^6$ cells per ml. The cell suspension obtained was placed into a 96-well microplate, into which was then added a normal mouse serum to a concentration of 10% by weight and then added 200 living cells of *Candida albicans*. The resulting mixture of the intraof peritoneal exudate cells and the Candida cells was incubated preliminarily for 3 hours in a 5% $CO_2$-incubator and subsequently transferred into a Sabouraud agar medium, followed by incubation for 48 hours at a temperature of 27°±1° C. After this incubation, number of the fungus cells was counted and the killing rate of the fungal cells was calculated according to the following equation:

$$\text{Killing Rate (\%)} = \frac{200 - (\text{number of surviving cells})}{200} \times 100$$

The above experiments were carried out in the same manner as above, using the physiological saline containing no test compound, and also using the chitin as the reference material.

The results of test in term of an average value±standard deviation are summarized in Table 2.

TABLE 2

Candidacidal activity of Peritoneal Exudate Cells in Mice Intraperitoneally Administered with the Chitin-oligomer or with Comparative Compounds

| Experiment No. | Test compound | Killing Rate in Candida cells (%) |
|---|---|---|
| 1 | Tetra-N-acetyl-chitotetraose | 71.3 ± 2.7 ($\underline{P}$ <0.01) |
| 2 | Penta-N-acetyl-chitopentaose | 80.6 ± 3.1 ($\underline{P}$ <0.01) |
| 3 | Hexa-N-acetyl-chitohexaose | 94.0 ± 3.4 ($\underline{P}$ <0.01) |
| 4 (Comparative test) | Chitin | 73.5 ± 3.5 ($\underline{P}$ <0.01 |
| Control test | None (Physiological saline) | 36.3 ± 6.0 |

EXAMPLE 6

This Example demonstrates that the administration of the water-soluble chitin-oligomer or chitosan-oligomer according to this invention can prolong the life span of mice lethally infected with a gram-positive bacterium, *Listeria monocytogenes* Serotype 4b.

An injectable solution as prepared similarly to the Examples 1–3 containing a chitin-oligomer or a chitosan-oligomer indicated in Table 3 was intraperitoneally injected into specific-pathogen-free (SPF) ddY mice (male, 5 weeks-aged, 8 mice per group) at a dosage of the active ingredient of 50 mg/kg per day at the times of 5, 3 and 1 days before the intraperitoneal inoculation of such a culture of the gram-positive bacteria as specified below.

After the immunopotentiating administration of the chitin-oligomer or the chitosan-oligomer, the treated mice were intraperitoneally inoculated with 0.1 ml of the cell suspension containing $6 \times 10^7$ cells of *Listeria monocytogenes* which had been prepared by incubating a slant culture of *L. monocytogenes* in a Brain Heart Infusion slant medium at 37° C., and incubating the resultant seed culture of the bacterium in a Trypticase Soy Broth medium at 37° C. for 24 hours under shaking. On the 15th day after the inoculation of bacteria, the rate of survival of the mice under test was evaluated.

These experiments were carried out in the same manner as above, using the mice not treated with the chitin-oligomer or chitosan-oligomer but receiving the inoculation of the bacterium (for the control test), and also using the mice treated with the chitin or chitosan and receiving the inoculation of bacterium for the comparison purpose.

The results of test are shown in Table 3.

TABLE 3

Effect of chitin- and chitosan-oligomers on Survival Rate of Mice Challenged with Viable Cells of *Listeria Momocytogenes* via Intraperitoneal Route

| Experiment No. | Test compound | Rate of Survival (%) |
| --- | --- | --- |
| 1 | Hexa-N-acetyl-chitohexaose | 100 |
| 2 | Chitohexaose | 87.5 |
| 3 (Comparative test) | Chitin | 66.6 |
| 4 (Comparative test) | Chitosan | 11.1 |
| Control test | None (Physiological saline) | 37.5 |

EXAMPLE 7

This Example demonstrates that the administration of the water-soluble chitin-oligomer according to this invention can prolong the life span of mice lethally infected with a gram-negative bacterium, *Pseudomonas aeruginosa*.

An injectable solution as prepared similarly to the Examples 1–3 containing a chitin-oligomer indicated in Table 4 was intraperitoneally injected into specific-pathogen-free (SPF) ddY mice (male, 5 weeks-aged, 8 mice per group) at a dosage of the active ingredient of 50 mg/kg per day at the times of 3, 2 and 1 days before the intravenous inoculation of such a culture of the gram-negative bacteria as specified below.

After the immunopotentiating administration of the chitin-oligomer or the chitosan-oligomer, the treated mice were intravenously inoculated with 0.1 ml of the cell suspension containing $1.2 \times 10^7$ cells of *Pseudomonas aeruqinosa* which had been prepared by incubating a slant culture of *P. aeruginosa* in a brain heart infusion slant medium at 37° C., and incubating the resultant seed culture of the bacterium in a plain bouillon medium at 37° C. for 24 hours under shaking. On the 15th day after the bacteria inoculation, the rate of survival of the mice under test was evaluated.

The experiments were carried out in the same manner as above, using the mice not treated with the chitin-oligomer or chitosan-oligomer but receiving the inoculation of the bacterium (for the control test), and also using the mice treated with the chitin and receiving the inoculation of the bacterium for the comparison purpose.

The result of test are shown in Table 4.

TABLE 4

Effect of chitin-oligomer on Survival Rate of Mice challenged with Viable Cells of *Pseudomonas aeruginosa* via Intraperitoneal Route.

| Experiment No. | Test compound | Rate of Survival (%) |
| --- | --- | --- |
| 3 (Comparative test) | Hexa-N-acetyl-chitohexaose<br>Chitin | 75<br>73.3 |
| Control test | None (Physiological saline) | 44 |

EXAMPLE 8

This Example demonstrates the activity of the chitin-oligomer to enhance the humoral antibody response.

An injectable solution as prepared similarly to the Examples 1–3 containing the chitin-oligomer indicated in Table 5 was intravenously injected into the tail of BALB/C mice (male, 4–6 weeks-aged, 6 mice per group) at a dosage of the active ingredient of 100 mg/kg once a day for the consecutive 3 days, totally 3 times. One day later, the treated mice were immunized with $1 \times 10^6$ sheep red blood cells (SRBC) as the antigen by intravenous injection. Four days later, the spleens were surgically removed from the mice under test, and the number of the antibody-forming cells per spleen was evaluated by the Jerne's hemolytic plaque assay method in term of the number of the plaque-forming cells, for the purpose of estimating the activity of the test compound to enhance the antibody formation in spleen.

This experiment was carried out in the same manner as above, using the physiological saline merely without the test compound.

The results of test expressed in term of an average value±standard deviation are summarized in Table 5.

TABLE 5

Effect of the chitin-oligomer on the humoral antibody response in mouse spleen ceels

| Experiment No. | Test Compound | Dosage of active ingredient (mg/kg × administration times) | Numer of the antibody forming cells per spleen ($\times 10^4$) |
| --- | --- | --- | --- |
| 1 | Hexa-N-acetyl-chitohexaose | 100 × 3 | 2.7 ± 0.3 ($P$ <0.01**) |
| Control test | None (Physiological saline) | 0.1 ml × 3 | 1.7 ± 0.08 |

EXAMPLE 9

This Example demonstrates that the chitin-oligomer can enhance the cellular immunity in mice.

An injectable solution as prepared similarly to the Examples 1–3 containing the chitin-oligomer or chitosan oligomer indicated in Table 6 was intraperitoneally administered into BALB/C mice (male, 4–6 weeks-aged, 6 mice per group) at a dosage of the active ingredient of 100 mg/kg once a day for the consecutive 3 days, totally 3 times. One day later, the treated mice were immunized with $1 \times 10^8$ sheep red blood cells (SRBC) as the antigen by injection of SRBC into the hind footpad. Four days later, the mice under test were administered again with SRBC by injection of $1 \times 10^8$ SRBC into the another hind footpad to estimate the response of the delayed type hypersensitivity (D.T.H.). An increased thickness of footpad was evaluated to assess the activity of the tested compound to enhance the cell-mediated (cellular) immunity.

This experiment was carried out in the same manner as above, but using the physiological saline without the test compound and also using the chitin for the positive control.

The results of test are shown in Table 6.

TABLE 6

Effect of the chitin-oligomer on the celluar immunity in mice immunized with SRBC

| Experient No. | Test Compound | Dosage of active ingredient (mg/kg × administration times | Increased thickness of footpad (× 0.1 mm) |
|---|---|---|---|
| 1 | Di-N-acetyl-chitobiose | 100 × 3 | 7.6 ± 0.89 |
| 2 | Tri-N-acetyl-chitotriose | 100 × 3 | 9.38 ± 0.78 ($P$ <0.05) |
| 3 | Tetra-N-acetyl-chitotetraose | 100 × 3 | 9.30 ± 0.80 ($P$ <0.05) |
| 4 | Penta-N-acetyl-chitopentaose | 100 × 3 | 8.03 ± 0.25 ($P$ <0.05) |
| 5 | Hexa-N-acetyl-chitohexaose | 100 × 3 | 10.5 ± 0.32 ($P$ <0.01) |
| 6 | Hepta-N-acetyl-chitoheptaose | 100 × 3 | 8.35 ± 0.97 |
| 7 (Comparative test 1) | Chitin | 100 × 3 | 9.28 ± 0.23 (0.01) |
| Control test | None (Physiological saline) | 0.1 ml × 3 | 6.93 ± 0.34 |

EXAMPLE 10

This Example demonstrates that the activity of the chitin-oligomer or chitosan-oligomer is growth-inhibitory to Sarcoma 180 solid tumor in mice.

ddY-Mice (male, SPF, 4–6 weeks-aged, 5 mice per group) were inoculated with Sarcoma 180 tumor cells ($1 \times 10^6$ per mouse) subcutaneously into the right groin of the mice. After seventh day as of the inoculation of the tumor cells, an injectable solution as prepared similarly to the Examples 1–3 containing the chitin-oligomer or the chitosan-oligomer indicated in Table 7 was intravenously injected into the tumor-bearing mice at a dosage of the active ingredient of 100 mg/kg once a day at an interval of one day during the consecutive 5 days, totally 3 times. After 23 days as of the inoculation of the tumor cells, the weight of the tumor was determined and the inhibition ratio (%) to the tumor growth was evaluated, as compared with the results of the control test. The control test was conducted using the mice which received the inoculation of the tumor cells and then received merely the injection of physiological saline without the test compound.

The results of test are shown in Table 7.

TABLE 7

Effect of the chitin- and chitosan-oligomers on the growth of Sarcoma 180 solid tumor in ddY-Mice

| Experiment No. | Test compound | Dosage of active ingredient (mg/kg × Administration times) | Average weight of tumor (g) | Inhibition Ratio (%) |
|---|---|---|---|---|
| 1 | Di-N-acetyl-chitobiose | 100 × 3 | 2.11 | 40 |
| 2 | Tri-N-acetyl-chitotriose | 100 × 3 | 1.05 | 70 |
| 3 | Hexa-N-acetyl-chitohexaose | 100 × 3 | 0.53 | 85 |
| 4 | Chitobiose | 100 × 3 | 1.83 | 48 |
| 5 | Chitotriose | 100 × 3 | 0.98 | 72 |
| 6 | Chitotetraose | 100 × 3 | 0.77 | 78 |
| 7 | Chitopentaose | 100 × 3 | 0.88 | 75 |
| 8 | Chitohexaose | 100 × 3 | 0.23 | 94 |
| Control test | None (Physiological saline) | 0.2 ml × 3 | 3.51 | 0 |

EXAMPLE 11

This Example also demonstrates that the activity of the chitin-oligomer or chitosan-oligomer is growth-inhibitory to Sarcoma 180 solid tumor.

ddy Mice (male, SPF, 4–6 weeks-aged, 7 mice per group) were inoculated with Sarcoma 180 tumor cells ($1 \times 10^6$ per mouse) subcutaneously into the right groin of the mice. After seventh day the inoculation of the tumor cells, an injectable solution was prepared similarly to the Examples 1–3 containing the chitin-oligomer or the chitosan-oligomer indicated in Table 8 was intravenously injected into the tumor-bearing mice at a dosage of the active ingredient of 100 mg/kg once a day at an interval of one day between the administrations of the test compound during the consecutive 9 days, totally 5 times of the administration. After 23 days the inoculation of the tumor cells, the weight of the tumor was determined and the inhibition ratio (%) to the tumor growth was evaluated, as compared with the results of the control test. The control test was conducted using the mice which received the inoculation of the tumor cells and then received merely the injection of physiological saline without the test compound.

The results of test are summarized in Table 8.

TABLE 8

Effect of the chitin- and chitosan-oligomers on the growth of Sarcoma 180 solid tumor in ddY Mice

| Experiment No. | Test compound | Dosage of active ingredient (mg/kg × administration times) | Inhibition Ratio (%) |
|---|---|---|---|
| 1 | Hexa-N-acetyl-chifohexaose | 100 × 5 | 100 |
| 2 | Chitohexaose | 100 × 5 | 98 |
| Control test | None (Physiological saline) | 0.2 ml × 5 | 0 |

EXAMPLE 12

This Example also demonstrates that the activity of the chitin-oligomer or chitosan-oligomer is growth-inhibitory to MM-46 solid tumor.

C3H/He Mice (male, SPF, 4–6 weeks-aged, 7 mice per group) were inoculated with MM-46 tumor cells ($1 \times 10^6$ per mouse) subcutaneously into the right groin of the mice. After seventh day the inoculation of the tumor cells, an injectable solution as prepared similarly to the Examples 1-3 containing the chitin-oligomer or the chitosan-oligomer indicated in Table 9 was intravenously injected into the tumor-bearing mice at a dosage of the active ingredient of 100 mg/kg once a day but at an interval of one day between the administrations of the test compound during the consecutive 9 days, totally 5 times of the administration. After 23 days the inoculation of the tumor cells, the weight of the tumor was determined and the inhibition ratio (%) to the tumor growth was evaluated, as compared with the results of the control test. The control test was conducted using the mice which received the inoculation of the tumor cells and then received merely the injection of physiological saline without the test compound.

The results of test are summarized in Table 9.

TABLE 9

Effect of the chitin- and chitosan-oligomers inhibitory to the growth of MM-46 solid tumor in C3H/He Mice

| Experiment No. | Test compound | Dosage of active ingredient (mg/kg × administration times) | Average weight of tumor (g) | Inhibition Ratio (%) |
|---|---|---|---|---|
| 1 | Hexa-N-acetyl-chitohexaose | 100 × 5 | 0.68 | 83 |
| 2 | Chitohexaose | 100 × 5 | 1.80 | 55 |
| Control test | None (Physiological saline) | 0.2 ml × 5 | 3.96 | 0 |

EXAMPLE 13

This Example also demonstrates the activity of the chitin-oligomer inhibitory to the growth of Meth-A tumor.

BALB/C Mice (male, SPF, 4-6 weeks-aged, 8 mice per group) were inoculated with Meth-A tumor cells ($1 \times 10^6$ per mouse) subcutaneously into the right groin of the mice. After 14th day the inoculation of the tumor cells, an injectable solution as prepared similarly to the Examples 1-3 containing the chitin-oligomer indicated in Table 10 was intravenously injected into the tumor-bearing mice at a dosage of the active ingredient of 100 mg/kg. After 23 days the inoculation of the tumor cells, the weight of the tumor was determined and the inhibition ratio (%) to the tumor growth was evaluated, as compared with the results of the control test. The control test was conducted using the mice which received the inoculation of the tumor cells and then received merely the injection of physiological saline without the test compound.

The results of test are summarized in Table 10.

TABLE 10

Effect of chitin-oligomer on the growth of Meth-A solid tumor in BALB/C Mice

| Experiment No. | Test compound | Dosage of active ingredient (mg/kg × administration times) | Average weight of tumor (g) | Inhibition Ratio (%) |
|---|---|---|---|---|
| 1 | Hexa-N-acetyl-chitohexaose | 100 × 1 | 5.42 | 44 |
| Control test | None (Physiological saline) | 0.2 ml × 1 | 9.59 | 0 |

EXAMPLE 14

This Example illustrates the production of the liposome preparation containing hexa-N-acetyl-chitohexaose as one of the chitin-oligomers available according to this invention.

A solution of 14 mg (17.5 μmol) of egg yolk lecithine (phosphatidylcholine), 6 mg (7.5 μmol) of phosphatidyl (15 μmol) of cholesterol in 5 ml of chloroform was placed together with one drop of tocopherol into a round-bottomed flask of 50 ml capacity. The flask with its contents was heated on an evaporator to distill off entirely the chloroform from said solution under reduced pressure. A small volume of chloroform was added into the flask and the residue remaining in the flask was dissolved in the chloroform added. The resulting solution was again distilled under well stirring by an electro-magnetic agitator, so that thin film mainly comprising the lecithine was formed on and over the inner wall surface of the flask, into which was then placed an aqueous solution of 20 mg of hexa-N-acetylchitohexaose dissolved in 2 ml of a phosphate buffer solution at such a rate that the total quantity of the lipids as charged was amounting to 20 μmol per ml of the aqueous solution of the chitin-oligomer. The content in the flask was further stirred by the electro-magnetic agitator, until there was formed a white-colored suspension of the liposomes. When the liposomes presented in said suspension were observed under electron-microscope, it was found that they were in the form of the multilamellar vesicles of about 1 to 10μ in diameter and that the aqueous solution of hexa-N-acetylchitohexaose was entrapped within the respective liposome vesicles.

The above-mentioned phosphate buffer solution employed had been prepared by dissolving 0.8 g of sodium chloride, 0.2 g of potassium chloride, 0.1 g of calcium chloride, 0.1 g of magnesium chloride hexahydrate, 2.9 g of disodium hydrogen phosphate 12-hydrate and 0.2 g of potassium dihydrogen phosphate in distilled water to a total volume of 1000 ml.

The above experiment was repeated but using tri-N-acetyl-chitotriose in place of the hexa-N-acetyl-chitohexaose. Similarly, the suspension of the liposomes containing the aqueous solution of tri-N-acetyl-chitotriose entrapped therein was prepared.

EXAMPLE 15

This Example demonstrates an increased activity of the liposomes containing hexa-N-acetyl-chitohexaose or tri-N-acetyl-chitotriose to inhibit the growth of Sarcome 180 tumor.

ddY Mice (male SPF, 4 weeks-aged, 6 mice per group) were inoculated with Sarcoma 180 tumor cells ($5 \times 10^6$ per mouse) subcutaneously into the right groin of the mice. After 7th day the inoculation of the tumor cells, the liposome suspension as prepared in the Example 14 of such quantity which was required to give the dosage of the active ingredient indicated in Table 11 was intravenously injected into the tail of the tumor-bearing mice. After 30 days from the inoculation of the tumor cells, the weight of the tumor was determined and the rate (in %) of the inhibition to the tumor growth was evaluated, as compared with the results of the control test.

The control test was conducted in such a way that the mice having received the inoculation of the tumor cells were treated with the aforesaid phosphate buffer solution only in place of the suspension of the liposomes containing hexa-N-acetyl-chitohexaose and the weight of the tumor was then measured (Control test No. 2). The above experiment was repeated but treating the tumor-bearing mice with a mere aqueous solution of hexa-N-chitohexaose (for comparison) or treating the tumor-bearing mice with the suspension of liposomes containing therein no hexa-N-acetyl-chitohexaose but containing merely the phosphate buffer solution entrapped therein (for control test No. 1).

The results of test are summarized in Table 11.

TABLE 11

Antitumor Effect of the chitin-oligomers Encapsuled in Liposome on Sarcoma 180 solid tumor in ddY-Mice

| Experiment No. | Tested Preparation | Dosage of active ingredient per day × times of dose | Average weight of tumor (g) | Inhibition Ratio (%) |
|---|---|---|---|---|
| 1 | Hexa-N-acetyl-chitohexaose encapsuled in Liposome | 100 mg/kg × 1 | 2.18 | 81 |
| 2 | Aqueous solution of hexa-N-acetyl-chitohexaose | 100 mg/kg × 1 | 9.55 | 19 |
| Control Test No. 1 | Liposomes containing merely the phosphate buffer solution | — | 11.68 | 0 |
| Control Test No. 2 | The phosphate buffer solution | — | 11.73 | 0 |

What we claim is:

1. A method for stimulating the immune response, which comprises administering intravenously an aqueous solution containing an immunopotentiatingly effective amount of a hexa-N-acetyl-chitohexaose, to a host animal of which the immunity is desired to be enhanced.

2. A pharmaceutical composition for treating tumor cells sensitive to the treatment with hexa-N-acetyl-chitohexaose in a mammalian animal, comprising as an active ingredient hexa-N-acetyl-chitohexaose in an amount effective to inhibit the growth of tumor cells, when intravenously administered to the animal, in association with a pharmaceutically acceptable carrier for the active ingredient.

* * * * *